United States Patent [19]

Elliott et al.

[11] Patent Number: 4,827,051
[45] Date of Patent: May 2, 1989

[54] PESTICIDES

[75] Inventors: Michael Elliott, Stevenage; Norman Janes, Luton; Richard L. Elliott, Leatherhead, all of England

[73] Assignee: National Research Development Corporation, London, England

[21] Appl. No.: 37,344

[22] Filed: Apr. 13, 1987

Related U.S. Application Data

[62] Division of Ser. No. 823,974, Jan. 30, 1986, Pat. No. 4,668,702.

[51] Int. Cl.$^4$ .................. C07C 33/46; C07C 21/24
[52] U.S. Cl. ............................. 568/812; 570/185
[58] Field of Search .................. 568/812; 570/185; 514/531

[56] References Cited

U.S. PATENT DOCUMENTS

| | | | |
|---|---|---|---|
| 2,813,131 | 11/1957 | Kundiger et al. | 570/185 |
| 3,179,640 | 4/1965 | Middleton | 568/812 |
| 4,557,871 | 12/1985 | Hatayama et al. | 568/812 |
| 4,668,701 | 5/1987 | Elliott et al. | 568/531 |
| 4,668,702 | 5/1987 | Elliott et al. | 514/531 |

FOREIGN PATENT DOCUMENTS 1586787  3/1981  United Kingdom ................ 570/185

Primary Examiner—Werren B. Lone
Attorney, Agent, or Firm—Oblon, Fisher, Spivak, McClelland & Maier

[57] ABSTRACT

Pesticidal compounds have the formula:

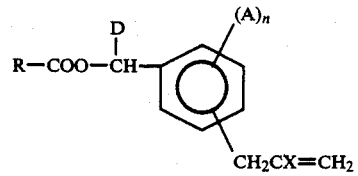

wherein
D represents hydrogen or a cyano group
X represents chlorine or bromine
A represents an alkyl group
n is 0 or an integer of 1–4 and
RCOO is the residue of an acid RCOOH whose α-cyano-3-phenoxybenzyl ester has pesticidal properties. They are prepared by esterification methods.

6 Claims, No Drawings

PESTICIDES

This is a division of application Ser. No. 06/823,974, filed Jan. 30, 1986 now U.S. Pat. No. 4,668,702, which is a continuation of U.S. Ser. No. 506,613, filed June 22, 1983, now abandoned.

This invention relates to pesticides and in particular to pesticidal compounds, the preparation of such compounds, intermediates for use in their preparation, compositions containing such compounds and the use of such compounds and compositions to control pests, for example pests present in soil.

Accordingly the present invention provides a compound of formula I

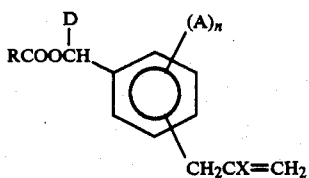

in which formula:
D represents hydrogen or a cyano group;
X represents chlorine or bromine
A represents an alkyl group (typically a $C_1$-$C_6$ alkyl group)
n is 0 to 4; and
RCOO is the residue of an acid RCOOH whose α-cyano-3-phenoxybenzyl ester has pesticidal properties.

Although the acid residue RCOO may derive from a wide variety of acids as hereinafter described, it is preferred that the acid residue is of a cyclopropane carboxylic acid such as chrysanthemic acid or a 2,2-dimethyl-3-(dihalovinyl)cyclopropane carboxylic acid, the 2,2-dimethyl-3-(dibromovinyl)cyclopropane carboxylic acid, especially when in the (IR,cis) form being of especial interest.

It is generally preferred, moreover, that D represents hydrogen and for the substituent group —$CH_2CX=CH_2$ to be disposed at the three or four position in the benzene ring with respect to the ester linkage. The substituent group is preferably disposed at the 4 position when D is H and at the 3 position when D is CN.

The following esters are of particular interest: 4-(2-chloroallyl)-benzyl [D=H, n=O, X=Cl], 3-(2-chloroallyl benzyl [D=H, n=O, X=Cl], α-cyano-3-(2-chloroallyl)benzyl [D=CN, n=O, X=Cl], particularly when of (IR)cis-3,-(2,2-dibromovinyl)cyclopropane carboxylic acid or (IR)-trans-chrysanthemic acid.

The group A, when present, typically represents methyl, and compounds in which two alkyl, e.g. methyl, groups are disposed at the 2,6 position in which the ring with respect to the ester link are of especial interest.

Esters I may be prepared by reaction of an acid $RCO_2H$ or an ester-forming derivative thereof with an intermediate of formula II

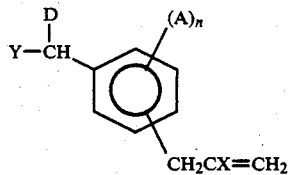

wherein Y represents a hydroxyl or halogen e.g. chlorine.

Intermediates of formula II are also included in a further aspect of the present invention.

Intermediate II in which Y represents —OH may be produced from aldehydes of formula IIA which are also included within the scope of the present invention.

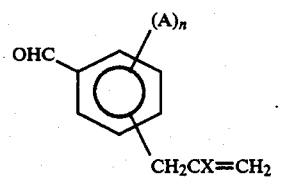

In accordance with a further aspect of the present invention, a compound II wherein Y represents OH and D represents hydrogen is produced from a compound IIA by reduction thereof. Such reduction may be hydride reduction using a reagent such as lithium aluminum hydride.

In accordance with a further aspect of the present invention, a compound II wherein Y represents OH and D represents a cyano group is produced from a compound IIA by treatment with an alkali metal cyanide. The reaction is typically conducted under acidic conditions in a homogenous reaction mixture comprising an aqueous organic solvent.

Intermediate II in which Y represents halogen and D represents hydrogen may be produced from intermediates II in which Y represents —OH and D represents hydrogen, in accordance with a further aspect of the present invention, by treatment of the latter intermediates with a halogenating reagent of the class employed for conversion of carboxylic acids to acyl halides e.g. $SO(hal)_2$, typically with pyridine or $P(hal)_3$, hal representing chlorine or bromine.

Compounds IIA may be produced in accordance with a further aspect of the present invention by reaction of a Grignard reagent of formula IIB

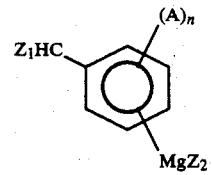

wherein $Z_2$ represents bromine or iodine and $Z_1$ represents a ketal group, typically ethylene ketal —$OCH_2$.$CH_2O$— with a complex formed between a compound Q—$CH_2$—$CX=CH_2$ wherein Q represents chlorine or bromine, typically chlorine, and a mixture of lithium and cuprous chlorides, followed by neutralization of the reaction mixture e.g. with $NH_4Cl$.

In the compounds of formula I, R represents the residue of a carboxylic acid RCOOH which is an acid known to be capable of forming pesticidal compounds when esterified with α-cyano-3-phenoxybenzyl alcohol. There are a large number of carboxylic acids that are known to form pesticidal compounds of this type and these carboxylic acids fall, for the most part, into two clearly defined groups. The first group is the cyclopropane carboxylic acids which are the compounds where R is a group of the formula:

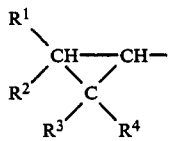   III

In formula III $R^3$ and $R^4$ will normally be an alkyl group, usually the same alkyl group, containing 1 to 4 carbon atoms and, as is well known in the art, dimethyl substitution normally gives high activity.

$R^2$ in formula III will normally be hydrogen or an alkyl group containing 1 to 4 carbon atoms and here the experience of the art indicates that $R^2$ will usually be hydrogen for maximum activity except in those compounds where $R^1$ is also an alkyl group, in which case $R^2$ preferably is an alkyl group, $R^1$, $R^2$, $R^3$ and $R^4$ all conveniently being the same alkyl group, e.g. methyl.

In formula III $R^1$ can be hydrogen or a substituted or unsubstituted acyclic or carbocyclic group. When $R^1$ is an unsubstituted hydrocarbyl group, it can be a straight chain or branched saturated or unsaturated acyclic or carbocyclic group such as an alkyl group, an alkenyl or alkadienyl group or a cycloalkyl, cycloalkylalkyl or cycloalkylalkenyl group. These hydrocarbyl groups preferably contain up to 10, particularly up to 6 carbon atoms.

When group $R^1$ is substituted, it is preferably one of the hydrocarbyl groups mentioned above which is substituted by one or more halogeno groups which may be fluorine, chlorine or bromine or by an alkoxy or oximino group or alkoxycarbonyl group, as in a group $R^1$ of particular interest of formula $-CH=CHCO_2R_x$ wherein $R_x$ represents an alkyl group typically containing 1 to 4 carbon atoms. When the substituents are two or more halogeno substituents, the halogeno substituents need not necessarily be the same halogen while when alkoxy groups are present, these preferably contain up to 4 carbon atoms and will normally be methoxy groups.

One particularly valuable structure for the group $R^1$ is of formula IV

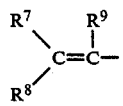   IV where $R^7$, $R^8$ and $R^9$, which may be the same or different, are each an alkyl group containing 1 to 4 carbon atoms, a trifluoromethyl group or a halogeno group, which may be the same or different and are preferably fluorine, chlorine or bromine. One or two of $R^7$, $R^8$ and $R^9$ may also represent hydrogen or a phenyl or substituted phenyl group. Alternatively, $R^7$ and $R^8$ may together form a straight or branched substituted or unsubstituted saturated or unsaturated divalent hydrocarbon chain which may be substituted by one or more hetero atoms e.g. O, N or S, so that $R^7$ and $R^8$ together with the carbon atom to which they are attached form a carbocyclic or heterocyclic ring which will preferably contain 5 to 7 ring atoms, optionally 1 or 2 carbon-to-carbon double bonds and optionally one or more alkyl ($C_1$-$C_4$) or halogeno substituents on the cycloaliphatic ring. Other compounds of interest are those in which R is a group of the structure

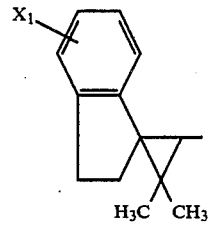

where the dotted line represents an optional double bond and $X_1$ represents H or halogen such as chlorine.

Specific cyclopropane carboxylic acids from which the compounds I of the present invention may be structurally derived include the following:

Chrysanthemic acid including particularly (1R)-trans chrysanthemic acid;
Pyrethric acid;
Dimethylcyclopropane carboxylic acid;
Trimethylcyclopropane carboxylic acid;
Tetramethylcyclopropane carboxylic acid;
2,2-Dimethyl-3-(cyclopentylidenemethyl)cyclopropane carboxylic acid;
2,2-Dimethyl-3-(2,2-dibromovinyl)cyclopropane carboxylic acid; particularly the (1R)-cis isomer thereof;
2,2-Dimethyl-3-(2,2-dichlorovinyl)cyclopropane carboxylic acid; particularly the (1R)-cis isomer thereof;
2,2-Dimethyl-3-(1,2,2,2-tetrabromoethyl)cyclopropane carboxylic acid;
2,2-Dimethyl-3-(1,2-dibromo-2,2-dichloroethyl)cyclopropane carboxylic acid;
2,2-Dimethyl-3-(2-chloro-3,3,3-trifluoropropenyl) cyclopropane carboxylic acid;
2,2-Dimethyl-3-(tetrahydro-2-oxo-thien-3-ylidenemethyl) cyclopropane carboxylic acid.

The second major class of carboxylic acids from which the esters of formula I may be structurally derived are the α-substituted aryl acetic acid esters. In these compounds R in formula I will normally be of the structure

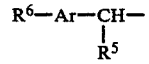   V wherein Ar represents a divalent aryl residue, $R^5$ represents a saturated or unsaturated straight chain or branched acyclic or cyclic hydrocarbon residue and $R^6$ represents hydrogen or one or more alkyl, alkoxy (including substituted alkoxy such as $OCF_3$ and $OCHF_2$) or halogeno substituents.

Ar will normally be an aryl residue based on a benzene ring although other aryl residues, e.g. polynuclear residues are also of interest. $R^5$ normally be a saturated straight or branched chain hydrocarbon group particularly an alkyl group containing up to 8 carbon atoms and it is often desirable that this alkyl group should contain at least one secondary carbon atom particularly when that secondary carbon atom is directly bonded to the carbon atom directly bonded to the $R^6$ substituted aryl group. Thus $R^5$ is preferably an isopropyl group or a secondary butyl group. $R^5$ can also be a cycloaliphatic residue, again preferably containing a secondary carbon atom located immediately adjacent to the carbon atom carrying the $R^6$ substituted phenyl group, e.g. $R^5$ may be a cyclopropyl group or an alkyl substituted cyclopropyl group. $R^5$ can also be a cycloalkylalkyl group.

$R^6$ is preferably one or more halogeno or halogen-containing substituents, e.g. F, Cl, Br or $OCHF_2$ or $OCF_3$ and, when more than one halogeno or halogen-containing substituent is present, they will normally be but are not necessarily the same halogen. When $R^6$ is an alkyl or alkoxy group, these preferably contain up to 4 carbon atoms and again, when more than one such group is present, they need not necessarily be the same groups. When only one substituent $R^6$ is present, it is preferably present in the para-position. When more than one $R^6$ substituent is present, the para-position is preferably substituted together with one or more of the ortho- and meta- positions.

Another class of carboxylic acids from from which the esters of the present invention may be structurally derived are α-substituted arylamino acetic acids of the type

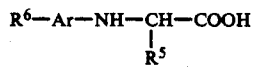

where $R^5$, $R^6$ and aryl are as defined above.

Specific α-substituted phenyl acetic acids from which esters of the formula I may be structurally derived include:
α-Isopropyl-p-chlorophenyl acetic acid;
α-Cyclopropyl-p-chlorophenyl acetic acid;
α-Cyclopropyl-p-methylphenyl acetic acid;
α-Isopropyl-p-(difluoromethoxy)-phenyl acetic acid;
α-Isopropyl-(2-chloro-4-trifluoromethyl anilino) acetic acid.

The compounds of the invention in which D is CN exhibit optical isomerism in that the carbon atom bearing the substituent D can exist in the R or S configuration and the present invention includes compounds in whch the configuration is substantially completely R or in which the configuration is substantially completely S or mixtures thereof.

Compounds of the invention in which R represents a substituted cyclopropane residue of formula III can exist in the form of both geometrical and optical isomers. This is because of the unsymmetrical substitution at $C_1$ and $C_3$ of the cyclopropane ring. Compounds of the present invention include those isomers in which the hydrogen atoms at $C_1$ and $C_3$ of the cyclopropane ring are substantially completely in the cis configuration or substantially completely in the trans configuration or mixtures thereof. The present invention also includes compounds in which the configuration at $C_1$ is substantially completely R or substantially completely S and mixtures thereof. In the compounds of the invention in which R represents a group of formula III, the optical configuration at $C_1$ and $C_3$ cannot vary independently of the geometrical configuration of the hydrogen atoms at $C_1$ and $C_3$ of the cyclopropane ring. The effect of this is that the configuration of the cyclopropane ring can be defined uniquely by specifying the optical configuration at $C_1$ and the geometrical configuration of the hydrogen atoms at $C_1$ and $C_3$ and, for definition purposes, we have adopted nomenclature of the form (1R)-cis, (1R)-trans etc. it being unnecessary to specify the optical configuration at $C_3$ which is fixed once the other two variables are defined. Adopting this nomenclature avoids the confusion which can arise by having to designate either R or S to the same optical configuration at $C_3$ depending upon the nature of the substituents on the cyclopropane ring and even those on the side chain.

When R is a group of formula III in which $R^1$ is a group of formula IV in which the substitution about the ethylenic bond is asymmetrical, that is to say $R^7 \neq R^8$ then the configuration of this part of the molecule can be substantially completely in the E form or substantially completely in the Z form or a mixture thereof.

When R is a group of formula V, the carbon atom to which $R^5$ is bonded can exist substantially completely in the S configuration or substantially completely in the R configuration or can be a mixture of the two forms.

The compounds of the present invention can be in the form of single isomers but, having regard to the fact that the compounds have at least one and frequently more than one center of asymmetry, the compounds of the invention will normally be in the form of isomer mixtures although these isomer mixtures can be optically active and/or substantially completely in one geometric form.

The compounds of the present invention can be prepared by an esterification involving the reaction of an alcohol of formula II or an esterifiable derivative thereof with a carboxylic acid of formula RCOOH or an esterifiable derivative thereof. It is usually convenient in practice to react an alcohol of formula II with an acyl chloride of formula RCOCl or to react a salt of the carboxylic acid, e.g. a silver or triethylammonium salt with a benzylhalide derivative, that is to say a monohaloallylbenzyl or cyanobenzyl halide which may be ring alkylated or to esterify the carboxylic acid with the alcohol in the presence of dicyclohexyl carbodiimide and a catalyst.

Alternatively, the esters of the invention can be prepared by transesterification by reacting a $C_1$-$C_6$ alkyl ester of the carboxylic acid with a benzyl alcohol of formula II in the presence of a basic transesterification catalyst. This method is not usually satisfactory where the molecule contains another base-sensitive residue, e.g. where the carboxylic acid is pyrethric acid.

One or more of the pesticidal esters of formula I can be formulated with an inert carrier or diluent to give pesticidal compositions and such compositions form a further aspect of the present invention. The compositions can be in the form of dusts and granular solids, wettable powders, mosquito coils and other solid preparations, or as emulsions, emulsifiable concentrates, sprays and aerosols and other liquid preparations after the addition of the appropriate solvents, diluents and surface-active agents.

Compositions formulated in a manner suitable for controlling soil pests typically by treatment of the soil are of especial interest. For this purpose compositions containing compounds I hereinbefore described are particularly suitable as they generally have lower molecular weights than many previously described pyrethroids, and it is envisaged that their relatively high vapour pressures allow them to diffuse through the soil.

The pesticidal compositions of the invention will normally contain from 0.001 to 25% by weight of the compound of formula I but the compositions can contain higher concentrations of active ingredient of formula I e.g. up to 96% for compositions to be sold as concentrates for dilution before use by the ultimate user.

The compositions of the invention can include diluents such as hydrocarbon oils, e.g. xylene or other petroleum fractions, water, anionic, cationic or non-ionic surface-active agents, anti-oxidants and other stabilizers as well as perfumes and colouring matters. These inert ingredients may be of the type and in proportions such as are conventionally used in pesticidal compositions containing pyrethroid-like compounds.

In addition to these inactive ingredients, the compositions of the present invention may contain one or more further active ingredients which may be other pesticidal compounds of the pyrethroid type or of other types and the composition may also include synergists of the type known to be capable of synergising the activity of natural pyrethrin and pyrethroid-like insecticides. Synergists of this type include piperonyl butoxide, tropital and sesamex.

The compounds of formula I can be used to control pest infestation in the domestic, horticultural or agricultural or medical, including veterinary, areas. The compounds or compositions of the invention can be used to combat pest infestation by treating pests or surfaces or environments susceptible to pest infestation with effective amounts of the active compounds of formula I or of compositions containing them. For example, they may be used in a domestic environment for spraying rooms to combat infestation with houseflies or other insects, they can be used for treatment of stored dry crops or cereals to combat infestation by insects or other pests, they can be used to spray growing crops, e.g. cotton or rice to combat infestation by common pests and they can be used in a medical or veterinary field, e.g. as a cattle spray to prevent or treat infestation by insects or other pests.

Although, as hereinbefore indicated, they are of particular interest for the disinfestation of soil to control pests such as the onionfly, *Delia antiqua*, or wheat bulb fly, *Delia coarctata* the compounds may find application in the control of a wide variety of pests including:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutitera spec.;

from the class of Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea madarae, Blattela germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Recticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Demalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolius* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aondiiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella,* Agrotis spp., Euxoa spp., Feltia spp., *Earias insulana*Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reciculana, Chroristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolntha melolntha, Amphimallon solstitialis* and *Costelytra zealandica;* from the order of the Hymenoptera, for example Diprion spp., Hoplacampa spp., Lasius spp., *Monomorium pharaonis* and Vespa spp., from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomopxys spp., Oestrus spp., Hypoderma spp., Tabanus spp., Tannia spp., *Bibio hortulanus, Oscinella frit,* Phorbia spp., *Pegomyia hyoscyami, Ceratitis capitat, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriphyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The invention is illustrated by the following Examples.

Temperatures are in °C.

EXAMPLE 1

4(2-chloroallyl)benzaldehyde

Dry Mg (0.58 g) under dry $N_2$ in a flask is covered with THF (5 ml) and a crystal of $I_2$ added. 5 ml of a solution of 4-bromobenzaldehyde ethylene acetal (5.0 g) in THF (25 ml) is added and kept until it becomes warm, when it is cooled to 15°, and the remainder of the acetal added over 15 min, then stirred for an additional 1 hour. A mixture of ground lithium chloride (0.35 g) and copper (I) chloride (0.70 g) dissolved in THF is prepared, treated with 1,2-dichloropropene ($CH_2Cl.CCl=CH_2$) (4.5 g) and cooled to −20°. The above Grignard solution (under moisture excluding conditions) is then added to this solution during 5 min, and allowed to warm to 20° with stirring for 16 hours. Saturated aqueous ammonium chloride is added and the organic layer evaporated under reduced pressure to a small residue, which is dissolved in THF (100 ml), cooled to −100°, treated with 3N HCl (50 ml), then stirred at 20° for 1 hour. The product is partitioned between ether and water, and the ether layer washed with $NaHCO_3$, $H_2O$ NaCl, dried ($MgSO_4$) and the residue chromatographed on florisil. The fraction eluted by 15% ether in petrol is collected and purified by preparative HPLC. Yield 0.50 g (13%) $n_D^{20}$ 1.5571.

EXAMPLE 2

4(2-chloroallyl)benzyl alcohol

The aldehyde (0.25 g) of Example 1 in ether (5 ml) is added to lithium aluminum hydride (0.03 g) in ether (5 ml), and the mixture stirred at 20° for 1 hour. After successive dropwise additions of water (30 μl), 15% NaOH (30 μl) and water (90 μl), the resulting clear ether layer (+ washings) is evaporated to a residue of 4(2-chloroallyl)benzyl alcohol yield 0.22 g (86%) $n_D^{20}$ 1.5504.

EXAMPLE 3

4(2-chloroallyl)benzyl(1R)cis-3(2,2-dibromovinyl)-2,2-dimethylcyclopropane carboxylate The alcohol of Example 2 (0.078 g) in benzene (2 ml) is added to (lR)cis 3-(2,2-dibromovinyl)2,2-dimethylcyclopropane carbonyl chloride (0.135 g) in benzene (3 ml). Pyridine (0.06 ml) is then added and the mixture stirred at 20° for 16 hours. This is chromatographed on florisil and the fraction eluted by 7% ether in petrol evaporated to a residue of 0.19 g (96%) ester, $n_D^{20}$ 1.5692.

EXAMPLES 4-6

Aldehydes of formula IIA are prepared by following the method described in Example 1, yield and refractive index being given in Table 1.

TABLE I

| | Aldehydes of formula IIA | | | | |
|---|---|---|---|---|---|
| Ex. No. | $(A)_n$ | Position of side chain | X | yield (%) | refractive index ($n_D^{20}$) |
| 4 | H | 3 | Cl | 15 | 1.5541 |
| 5 | H | 3 | Br | 29 | 1.5780 |
| 6 | H | 4 | Br | 22 | 1.5777 |

EXAMPLES 7-9

Alcohols of formula II are prepared by following the method described in Example 2, the yield and refractive index being given in Table II.

TABLE II

| | Alcohols of formula II | | | | |
|---|---|---|---|---|---|
| Ex. No. | $(A)_n$ | D | Position of side chain | X | yield (%) | refractive index ($n_D^{20}$) |
| 7 | H | H | 3 | Cl | 86 | 1.5524 |
| 8 | H | H | 3 | Br | 97 | 1.5699 |
| 9 | H | H | 4 | Br | 80 | 1.5729 |

EXAMPLE 10

4,-(2-chloroallyl)benzaldehyde cyanohydrin

The aldehyde of Example 1 (0.25 ) and potassium cyanide (0.5 g) in water (1.4 ml) and THF (5 ml) are treated with 40% sulphuric acid (1.5 ml) with cooling to 3° to 8°. After 1 hour at 20°, the reaction mixture is extracted with ether which is washed, dried and evaporated to a residue of α-cyano-4-(2-chloroallyl)benzyl alcohol (0.24 g, 83%) $n_D^{20}$ 1.5463.

EXAMPLES 11-13

Cyanohydrins of formula II are prepared by following the method described in Example 10, the yield and refractive index being given in Table III.

TABLE III

| Ex. No. | $(A)_n$ | D | Position of side chain | X | yield (%) | refractive index ($n_D^{20}$) |
|---|---|---|---|---|---|---|
| 11 | H | CN | 3 | Cl | 83 | 1.5442 |
| 12 | H | CN | 3 | Br | 97 | 1.5611 |
| 13 | H | CN | 4 | Br | 98 | 1.5593 |

EXAMPLES 14-28

Esters of formula I are prepared by following the method described in Example 3.

The pesticidal activity is assessed against houseflies and mustard beetles by using the following techniques:

Houseflies (*Musca domestica*)

Female flies are treated on the thorax with a one microliter drop of insecticide dissolved in acetone. Two replicates of 15 flies are used at each does rate and 6 dose rates are used per compound under test. After treatment, the flies are maintained at a temperature of 20°±1° and kill is assessed 24 and 48 hours after treatment. $LD_{50}$ values are calculated in micrograms of insecticide per fly and relative toxicities are calculated from the inverse ratios of the $LD_{50}$ values (see Sawicki et al., Bulletin of the World Health Organization, 35, 893, (1966) and Sawicki et al., Entomologia and Exp. Appli. 10 253, (1967)).

Mustard Beetles (*Phaedon cochleariae Fab*)

Acetone solutions of the test compound are applied ventrally to adult mustard beetles using a micro drop applicator. The treated insects are maintained for 48 hours after which time kill is assessed. Two replicates of 40 to 50 mustard beetles are used at each dose level and 5 dose levels are used for each compound. Again, $LD_{50}$ values are calculated and relative potencies are calculated from the inverse ratios of $LD_{50}$ (see Elliott et al., J. Sci. Food Agric. 20, 561, (1969).

Relative potencies are calculated by comparison with 5-benzyl-3-furylmethyl (1R)-trans-chrysanthemate (Bioresmethrin) which is one of the more toxic chrysanthemate esters known to house flies and mustard beetles, its toxicity being about 24 times that of allethrin to houseflies and 65 times that of allethrin to mustard beetles.

TABLE IV

Esters of Formula I
Acid residue RCOO—: A1 = (1R)-trans chrysanthemyl
A2 = (1R)-cis-3-(2,2-dibromovinyl)-2,2-dimethylcyclopropane carboxyl
Relative Potency to Houseflies and Mustard Beetles (Bioresmethrin = 100) given under HF and MB respectively

| Example No. | $(A)_n$ | Acid residue | D | Position of side chain | X | Yield (%) | Refractive index ($n_D^{20}$) | Relative potency HF | MB |
|---|---|---|---|---|---|---|---|---|---|
| 3 | H | A2 | H | 4 | Cl | 96 | 1.5692 | 240 | 9 |
| 14 | H | A1 | H | 3 | Cl | 69 | 1.5280 | 5 | 0.8 |
| 15 | H | A2 | H | 3 | Cl | 79 | 1.5703 | 31 | 7 |
| 16 | H | A1 | H | 4 | Cl | 75 | 1.5260 | 64 | 2 |
| 17 | H | A1 | CN | 3 | Cl | 65 | 1.5245 | 9 | 6 |
| 18 | H | A2 | CN | 3 | Cl | 79 | 1.5606 | 29 | 17 |
| 19 | H | A1 | CN | 4 | Cl | 73 | 1.5271 | 1 | 0.3 |
| 20 | H | A2 | CN | 4 | Cl | 75 | 1.5535 | 4 | 1 |
| 21 | H | A1 | H | 3 | Br | 61 | 1.5353 | 5 | 0.6 |
| 22 | H | A2 | H | 3 | Br | 84 | 1.5765 | 82 | 4 |
| 23 | H | A1 | H | 4 | Br | 58 | 1.5341 | 12 | 1 |
| 24 | H | A2 | H | 4 | Br | 90 | 1.5761 | 89 | 5 |
| 25 | H | A1 | CN | 3 | Br | 71 | 1.5349 | 4 | 3 |
| 26 | H | A2 | CN | 3 | Br | 82 | 1.5729 | 8 | 6 |
| 27 | H | A1 | CN | 4 | Br | 61 | 1.5305 | 0.8 | non-toxic |
| 28 | H | A2 | CN | 4 | Br | 66 | 1.5670 | 0.9 | 0.7 |

We claim:
1. The compound of the formula:

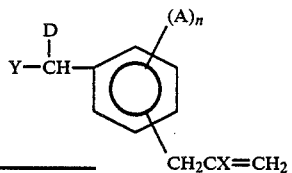

wherein:
Y represents OH or a halogen atom;
D represents hydrogen or a cyano group;
A represents a $C_{1-6}$ alkyl group;
X represents chlorine or bromine; and
n is 0 or an integer of from 1 to 4.

2. The compound of claim 1, wherein —CH$_2$CX═CH$_2$ is at the 3- or 4-position.

3. The compound of claim 2, wherein D represents H and —CH$_2$CX═CH$_2$ is at the 4-position.

4. The compound of claim 2, wherein D represents CN and —CH$_2$CX═CH$_2$ is at the 3-position.

5. The compound of claim 1, wherein n is 0.

6. The compound of claim 1, wherein said compound is 4-(2-chloroallyl)benzylalcohol.

* * * * *

UNITED STATES PATENT AND TRADEMARK OFFICE
CERTIFICATE OF CORRECTION

PATENT NO. : 4,827,051

DATED : May 02, 1989

INVENTOR(S) : Michael Elliott, et al

It is certified that error appears in the above-identified patent and that said Letters Patent is hereby corrected as shown below:

On the title page, item [30], the priority information has been omitted, it should read as follows:

--Jun. 28, 1982 [GB] United Kingdom ............8218621--

Signed and Sealed this

Nineteenth Day of December, 1989

Attest:

JEFFREY M. SAMUELS

*Attesting Officer*      *Acting Commissioner of Patents and Trademarks*